(12) United States Patent
Wood et al.

(10) Patent No.: US 8,473,033 B2
(45) Date of Patent: Jun. 25, 2013

(54) METHOD AND SYSTEM FOR DETERMINING TRACHEAL AND LOCATION INFORMATION FOR A TRACHEAL TUBE

(75) Inventors: Lockett E. Wood, Lyons, CO (US); Sarah Hayman, Boulder, CO (US)

(73) Assignee: Covidien LP, Mansfield, MA (US)

( * ) Notice: Subject to any disclaimer, the term of this patent is extended or adjusted under 35 U.S.C. 154(b) by 1034 days.

(21) Appl. No.: 12/485,990

(22) Filed: Jun. 17, 2009

(65) Prior Publication Data
US 2010/0319702 A1 Dec. 23, 2010

(51) Int. Cl.
*A61M 16/04* (2006.01)
(52) U.S. Cl.
USPC ....... 600/424; 600/407; 600/529; 128/207.14
(58) Field of Classification Search
None
See application file for complete search history.

(56) References Cited

U.S. PATENT DOCUMENTS

| | | | |
|---|---|---|---|
| 3,931,822 A | 1/1976 | Marici |
| 4,285,340 A | 8/1981 | Gezari et al. |
| 4,526,196 A | 7/1985 | Pistillo |
| 4,552,558 A | 11/1985 | Muto |
| 4,565,194 A | 1/1986 | Weerda et al. |
| 4,630,606 A | 12/1986 | Weerda et al. |
| 4,898,168 A | 2/1990 | Yule |
| 4,943,770 A | 7/1990 | Ashley-Rollman |
| 5,099,845 A | 3/1992 | Besz et al. |
| 5,218,970 A | 6/1993 | Turnbull et al. |
| 5,235,973 A | 8/1993 | Levinson |
| 5,257,636 A | 11/1993 | White |
| 5,361,753 A | 11/1994 | Pothmann et al. |
| 5,546,935 A | 8/1996 | Champeau |
| 5,560,351 A | 10/1996 | Gravenstein et al. |
| 5,591,130 A | 1/1997 | Denton |
| 5,740,796 A | 4/1998 | Skog |
| 5,752,921 A | 5/1998 | Orr |
| 5,785,051 A | 7/1998 | Lipscher |
| 5,819,723 A | 10/1998 | Joseph |
| 5,885,248 A | 3/1999 | Denton |
| 5,906,204 A | 5/1999 | Beran et al. |
| 6,102,041 A | 8/2000 | Boussignac |
| 6,253,770 B1 | 7/2001 | Acker et al. |
| 6,263,230 B1 | 7/2001 | Haynor et al. |
| 6,315,739 B1 | 11/2001 | Merilainen et al. |
| 6,530,898 B1 | 3/2003 | Nimkar et al. |
| 6,647,984 B1 | 11/2003 | O'Dea |

(Continued)

FOREIGN PATENT DOCUMENTS

| WO | 9422518 | 10/1994 |
|---|---|---|
| WO | WO 94/22518 | * 10/1994 |

OTHER PUBLICATIONS

International Search Report PCT/US2010/0038529, 5 pages, mailed Nov. 8, 2010.

(Continued)

*Primary Examiner* — Long V. Le
*Assistant Examiner* — Farshad Negarestan

(57) ABSTRACT

According to various embodiments, a tracheal tube may include signal sources for providing information at various locations on the tube or in an inflated cuff. The signals from the signal sources may be triangulated to determine the location of the tube in relation to a reference point on the body. The location information may provide an indication as to whether or not the tracheal tube is properly placed within the trachea.

25 Claims, 6 Drawing Sheets

U.S. PATENT DOCUMENTS

| | | | |
|---|---|---|---|
| 6,926,670 | B2 | 8/2005 | Rich et al. |
| 2002/0066450 | A1 | 6/2002 | Bonutti |
| 2007/0137652 | A1 | 6/2007 | Qureshi et al. |
| 2009/0036790 | A1* | 2/2009 | Landesberg et al. ........... 600/529 |
| 2011/0197888 | A1* | 8/2011 | Deutsch et al. .......... 128/204.23 |

OTHER PUBLICATIONS

Lomholt, N., A Device for Measuring the Lateral Wall Cuff Pressure of Endotracheal Tubes, Acta Anaesthesiologica Scandinavica, Dec. 1992, pp. 775-778, Issue 36.

Pollard, Richard. J. MD et al., Endotracheal Tube Location Verified Reliably by Cuff Palpation, Anesthesia and Analgesia, 1995, pp. 135-138.

Roberts, James R. et al., Proper Depth of Placement of Oral Endotracheal Tubes in Adults Prior to Radiographic Confirmation, Academic Emergency Medicine, Jan. 1995, pp. 20-24, vol. 2, No. 1.

Guttmann, Josef PhD et al., Continuous Calculation of Intratracheal Pressure in the Presence of Pediatric Endotracheal Tubes, Critical Care Medicine, Apr. 2000, pp. 1-21, vol. 28, Issue 4.

Karasawa, Fujio. MD et al., Profile Soft-Seal Cuff, a New Endotracheal Tube, Effectively Inhibits an Increase in the Cuff Pressure through High Compliance Rather than Low Diffusion of Nitrous Oxide, Anesthesia and Analgesia, Dec. 2001, pp. 140-144, Issue 92.

Sondergaard, Soren. et al., Direct Measurement of Intratracheal Pressure in Pediatric Respiratory Monitoring, Pediatric Research, Dec. 2002, vol. 51, No. 3.

Najafi, Nader, MEMS Implant for Cardiovascular Applications, The Newsletter of Tools and Products in Micro and Nanotechnology-Micro Nano, Sep. 2003, p. 1, vol. 8, No. 9.

Dullenkopf, A. et al., Air Leakage Around Endotracheal Tube Cuffs, European Journal of Anaesthesiology, Dec. 2004, pp. 448-453, Issue 21.

Horisberger, T. et al., Measurement of Tracheal Wall Pressure: A Comparison of Three Different in Vitro Techniques, Journal of the Association of Anaesthetists of Great Britain and Ireland, Dec. 2008, pp. 418-422, Issue 63.

Khazin, Vadim MD et al., Gastroesophageal Regurgitation during Anesthesia and Controlled Ventilation with Six Airway Devices, Journal of Clinical Anesthesia, Dec. 2008, pp. 508-513, Issue 20.

Wireless, Batteryless Implantable Medical Products, Integrated Sensing Systems, Jan. 2009, pp. 1-5.

Orr, Joseph A., Tracheal Pressure Controller for Ventilators, National Institute of Allergy and Infectious Diseases, Jun. 2010, pp. 1-7.

Monitoring of Intubation and Ventilation During Resuscitation, http://clinicaltrials.gov/ct2/show/NCT00204217, ClinicalTrials.gov, Aug. 2010, pp. 1-3.

Schwarz, Uwe MD, Validation of Supra-Sternal Tube-Tip Palpatation (SSTTP), http://clinicaltrials.gov/ct2/show/NCT00690508, ClinicalTrials.gov, Aug. 2010, pp. 1-4.

Karsli, Cengiz, Head Movement Effect on Different Tracheal Tubes, http://clinicaltrials.gov/ct2/show/NCT00687583, ClinicalTrials.gov, Aug. 2010, pp. 1-3.

Gravenstein, D. et al., Breakthroughs in Endotracheal Tube Design and Verification of Tracheal Placement, University of Florida, Office of Technology Licensing, pp. 1-2.

* cited by examiner

METHOD AND SYSTEM FOR DETERMINING TRACHEAL AND LOCATION INFORMATION FOR A TRACHEAL TUBE

BACKGROUND

The present disclosure relates generally to medical devices and, more particularly, to airway devices, such as tracheal tubes.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

For example, a patient may be intubated by insertion of an endotracheal tube through the patient's mouth and into the trachea. Often, such intubation procedures may be performed during medical emergencies or during critical care situations. As such, healthcare providers may balance a desire for speed of intubation with a desire for accurate placement of the tube within the trachea. However, proper placement of a tracheal tube may be complex. In certain situations, placement may be aided with visualization of the trachea performed during laryngoscopy. During an intubation procedure, a practitioner may employ a lighted laryngoscopy during introduction of the endotracheal tube. However, often the visualization of the trachea is poor because of patient secretions that may obscure the laryngoscopy. In addition, such visualization during introduction of the tube may not account for ongoing changes in the tube's position within the trachea that may occur when a patient coughs, which may dislodge a tube from its desired location, or when a patient is jostled or moved within a care setting, which may change the position or angle of the tube within the trachea.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

Figure 1:
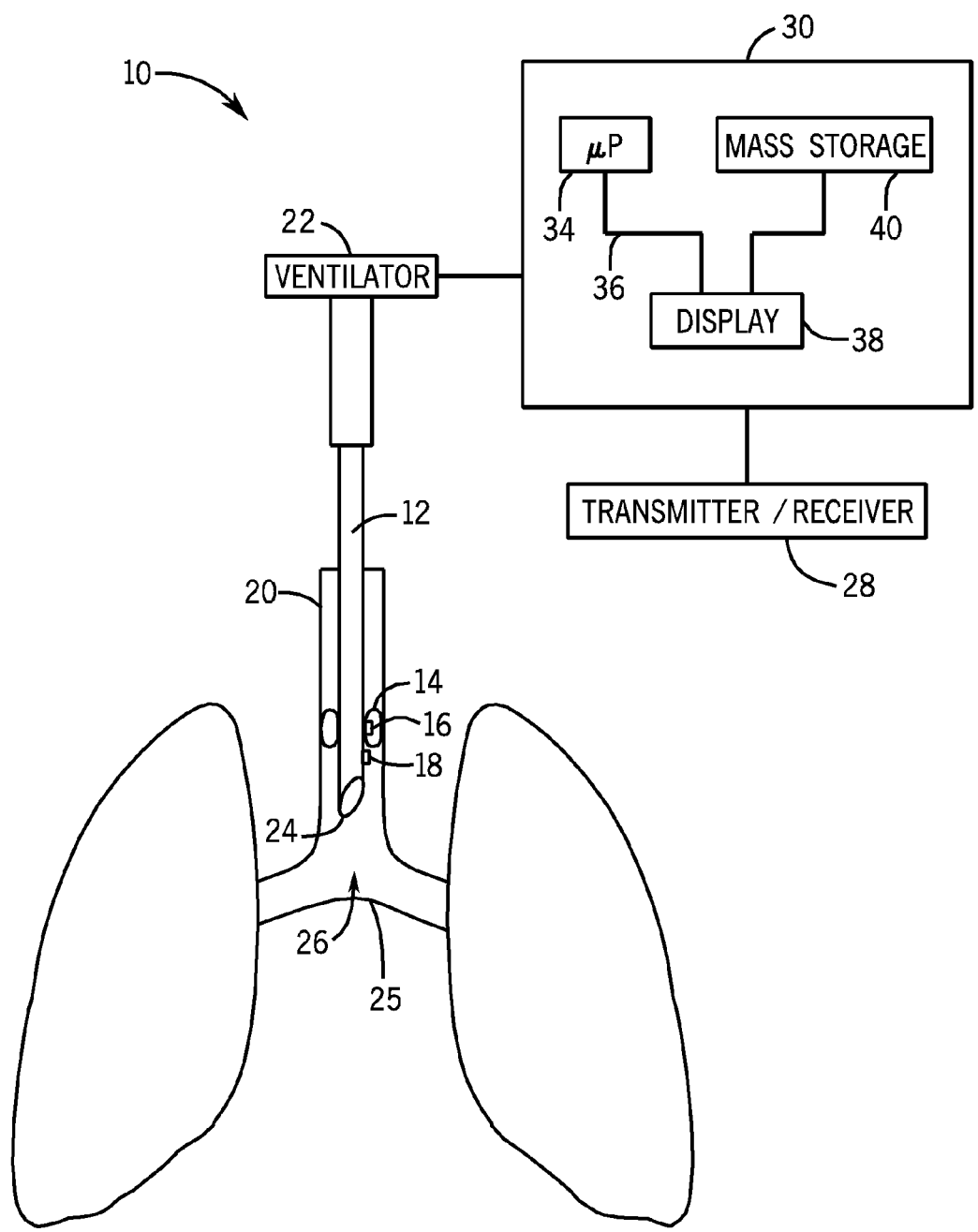
FIG. 1 illustrates an exemplary system including an endotracheal tube with a first pressure transducer and a second pressure transducer according to presently contemplated embodiments.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube may be used to seal a patient's airway and provide positive pressure to the lungs when properly inserted into a patient's trachea. Positioning the tracheal tube at a desired position within the trachea, for example during endotracheal intubation, may improve the performance of the tracheal tube and reduce clinical complications. In particular, the distal inserted end of the endotracheal tube may be positioned in the patient's trachea at a location substantially between the patient's vocal cords and carina. If the tube cuff is not inserted far enough past the vocal cords, for example, the tube may become more easily dislodged. If the tube is inserted too far into the trachea, such as past the carina, then the tube may only function to adequately ventilate one of the lungs, rather than both. Thus, proper placement of the distal tip of the tube may result in improved ventilation to the patient.

Described herein are tracheal tubes and systems for facilitating proper placement of the tracheal tube relative to certain anatomical structures in and around the patient's airway and trachea. Such tracheal tubes may include a plurality of signal sources that may provide signals to a receiver or a transceiver that may be located outside the body. By triangulating the signals, the location of the signal sources relative to a reference point, for example an anatomical structure, may be determined. A healthcare provider may then use the information about the location of the tracheal tube relative to the anatomical structures (e.g., a patient's sternal notch or a carina) to determine whether the tube is properly placed or whether the position of the tube should be adjusted.

The signal sources may also provide information related to the operation of the tube. For example, a clinician may monitor the pressure at various points along the airway to determine if respiratory gases are reaching the patient at adequate levels. In order to facilitate the pressure monitoring, pressure transducers may be located at appropriate locations on the tracheal tube. A pressure transducer may be located at a distal tip of the tracheal tube to sample gases in the sealed tracheal space. Because this space is contiguous with the lung space, the trachea pressure may serve as a surrogate for pressure in the lungs. In addition, a pressure transducer may be located within an inflatable cuff associated with the tube. Pressure information from inside the cuff may be used to monitor the quality of the cuff's seal against the tracheal walls. In addition, in certain embodiments, cuff pressure may be used to estimate pressure in the trachea.

While certain types of pressure measurements may be made with pressure transducers that are located outside the tube, but are in fluid communication with the cuff or the trachea, certain types of pressure transducers may be placed directly on or in the tube. For transducers placed directly on the tube, the signals from the transducers may provide information about the pressure at the locations where the transducers are disposed. In addition, the signals may also be used to determine placement information about the tube. The signal from a first pressure transducer at a distal end of a tracheal tube may be triangulated with a signal from a second pressure transducer at a different location, for example in a cuff, to determine the location of one or both of the pressure transducers. In addition, their locations may be determined relative to a reference point. For example, the signals may be triangulated relative to a point on the body. In such a manner, the location of the pressure transducers relative to an anatomical structure may be estimated. Accordingly, pressure transducers may provide pressure information as well as location information.

The disclosed tracheal tubes, systems, and methods may be used in conjunction with any appropriate medical device, including without limitation a feeding tube, an endotracheal tube, a tracheotomy tube, a circuit, an airway accessory, a connector, an adapter, a filter, a humidifier, a nebulizer, nasal cannula, or a supraglottic mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

FIG. 1 shows an exemplary tracheal tube system 10 that has been inserted into the trachea of a patient. The system 10 includes a tracheal tube 12, shown here as an endotracheal tube, with an inflatable balloon cuff 14 that may be inflated to form a seal against the tracheal walls 20. The tracheal tube 12 may also include two or more signal sources located at different points along the tube 12. By way of example, the tracheal tube 12 may include a first signal source 16 located within the inflated area of the cuff 14 and a second signal source 18 located at or near the distal end 24, which may be a certain distance from a carina 25. Other arrangements are also contemplated, including arrangements with three, four, or more signal sources disposed at any suitable point in or on the tube 12 or cuff 14. The tracheal tube 12 may be coupled to a medical device, such as a ventilator 22. In addition, the system 10 may include a receiver or transmitter/receiver (e.g., a transceiver) 28 to receive signals from signal source 16 and signal source 18 and that is operatively connected to a monitor 30. The pressure signal source 16 and pressure signal source 18 generate signals that may be communicated wirelessly to the associated receiver 28.

The signals generators may be RF tags that generate RF signals capable of being picked up by the receiver 28. In certain contemplated embodiments, one or more of the signal sources may include wireless sensors that are capable of providing information about the immediate environment, such as pressure transducers, temperature sensors, or optical sensors capable of monitoring blood oxygen or carbon dioxide levels. The pressure in the tracheal space 26 may be monitored by signal source 18, which is open to the tracheal space 26, while the pressure in the cuff 14 may be monitored by pressure signal source 16.

The system 10 may also include devices that facilitate positive pressure ventilation of a patient, such as the ventilator 22, which may include any ventilator, such as those available from Nellcor Puritan Bennett LLC. The system may also include a monitor 30 that may be configured to implement embodiments of the present disclosure to determine pressures based upon the pressure detected within the cuff 14 or at the distal end 24 of the tube 12. In addition, the monitor 30 may be configured to calculate certain placement parameters based on triangulation of the signals from signal source 16 and transducer 18. It should be understood that the monitor 30 may be a stand-alone device or may, in certain embodiments, be integrated into a single device with, for example, the ventilator 22.

The monitor 30 may include processing circuitry, such as a microprocessor 32 coupled to an internal bus 34 and a display 36. In one embodiment, the monitor 30 may be configured to communicate with the receiver 28, either through a cable connection or wirelessly to obtain the received signals from the signal source 16 and transducer 18. The receiver 28 or the signal source 16 and signal source 18 may also provide calibration information to the monitor 30. Calibration information may be stored on a barcode or a separate memory circuit, such as a memory circuit associated with a cable connector. The information may then be stored in mass storage device 40, such as RAM, PROM, optical storage devices, flash memory devices, hardware storage devices, magnetic storage devices, or any suitable computer-readable storage medium. The information may be accessed and operated upon according to microprocessor 32 instructions. Calibration information may also be used in calculations for estimating of pressure in the lungs where the signal sources provide pressure information. The monitor 30 may be configured to provide indications of the lung pressure, such as an audio, visual or other indication, and may be configured to communicate the pressure information or location information to another device, such as the ventilator 22.

Figure 2A:
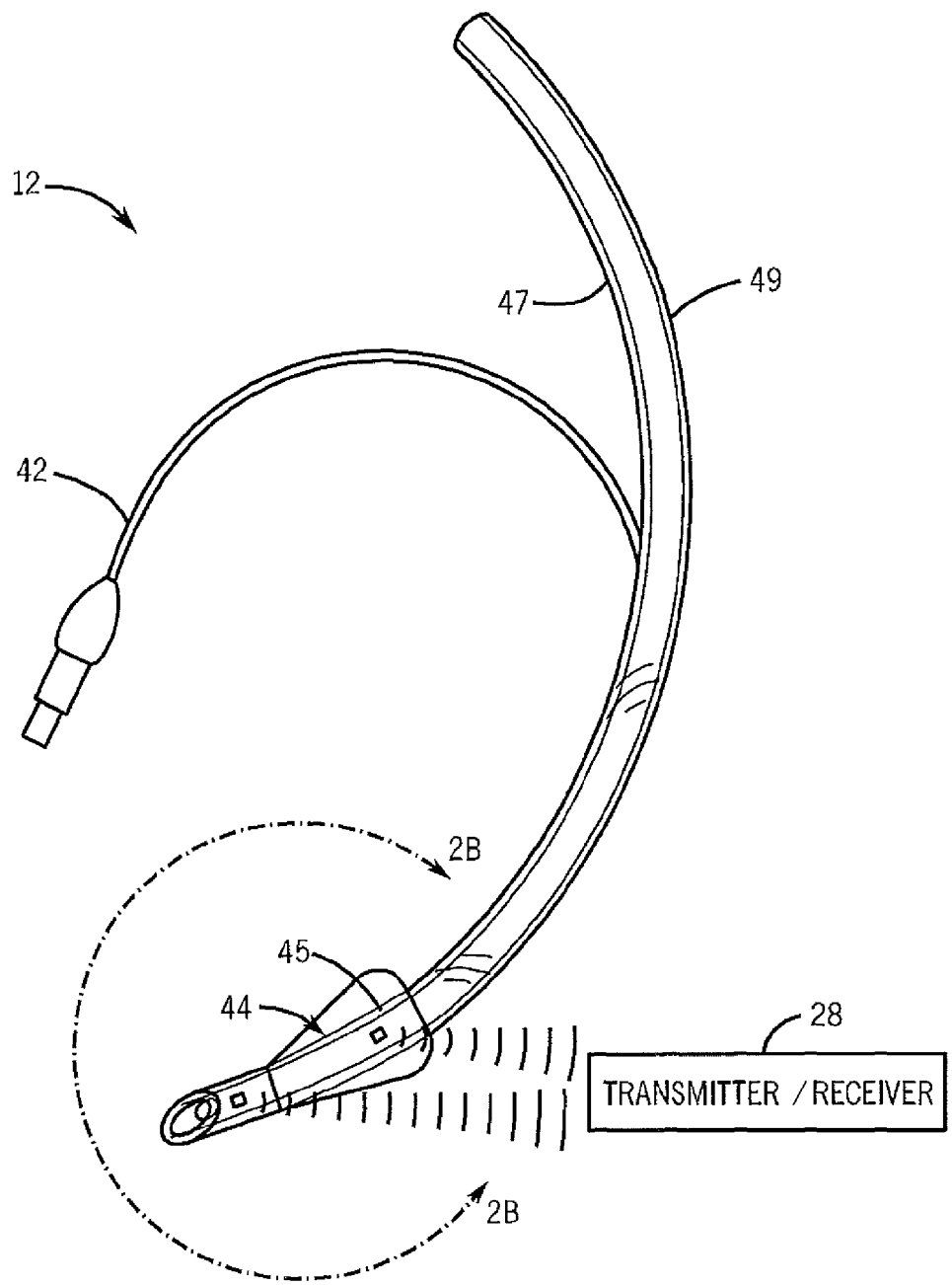
FIG. 2A is a perspective view of an endotracheal tube that may be used in conjunction with the system of FIG. 1 according to embodiments.
Figure 2B:
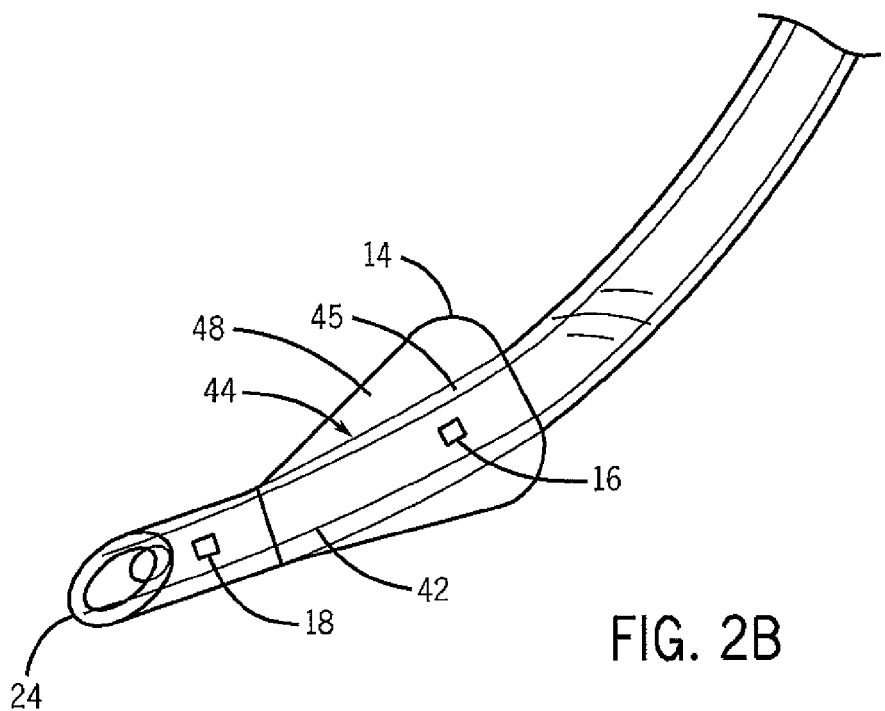
FIG. 2B is a detail view of the distal end and cuff area of the tube.

FIG. 2A is a perspective view of an exemplary tracheal tube 12 according to certain presently contemplated embodiments. The tube 12 may include a cuff 14 that may be inflated via inflation lumen 42. As shown in more detail in the detail view in FIG. 2B, the cuff 14 may define an inflated space 48 that substantially surrounds the signal source 16, which may be embedded in or otherwise attached to an exterior surface 44 of a wall 45 of the tube 12. Signal source 18 may similarly be embedded or otherwise attached to an exterior surface 44 of a wall 45 of the tube 12 on or adjacent to a distal end 24. The tube 12 may have a generally curved shape, such certain parts of the wall 45 are located on the inside face 47 of the curve while other portions of the wall 45 are located on the outside 49 of the curve.

The signal source 16 and signal source 18 may be configured to communicate wirelessly, such as through radio frequency, with the receiver 28. For example, the pressure signal source 16 and pressure signal source 18 may be wireless implantable sensors, such as those available from ISSYS (Ypsilanti, Mich.). Generally, implanted medical devices may communicate in the 402-405 MHz frequency band for medical implant communications service (MICS). In certain embodiments, the signal sources 16 and 18 may communicate at different frequencies so that their respective signals may be distinguished from one another. In certain embodiments, one or more of the signal sources may include a suitable pressure sensor that may be integrated into or onto the exterior wall of the tube 12. For example, the signal source 16 may be a piezoelectric pressure sensor.

To minimize power consumption, the signal sources 16 and 18 may be passive, e.g., they may remain quiescent until they detect a signal, such as a signal from a transmitter associated with receiver 28. In other embodiments, signal sources 16 and 18 may be active and capable of generating signals in the absence of a receiver 28. In such embodiments, a power source (e.g., a battery) may be associated with the signal sources 16 and 18.

The tube 12 and the cuff 14 may be formed from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In one embodiment, the cuff 14 may be generally sized and shaped as a high volume, low pressure cuff that may be designed to be inflated to pressures between about 15 cm $H_2O$ and 30 cm $H_2O$. The system 10 may also include a respiratory circuit (not shown) connected to the endotracheal tube 12 that allows one-way flow of expired gases away from the patient and one-way flow of inspired gases towards the patient. The respiratory circuit, including the tube 12, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

Figure 3:
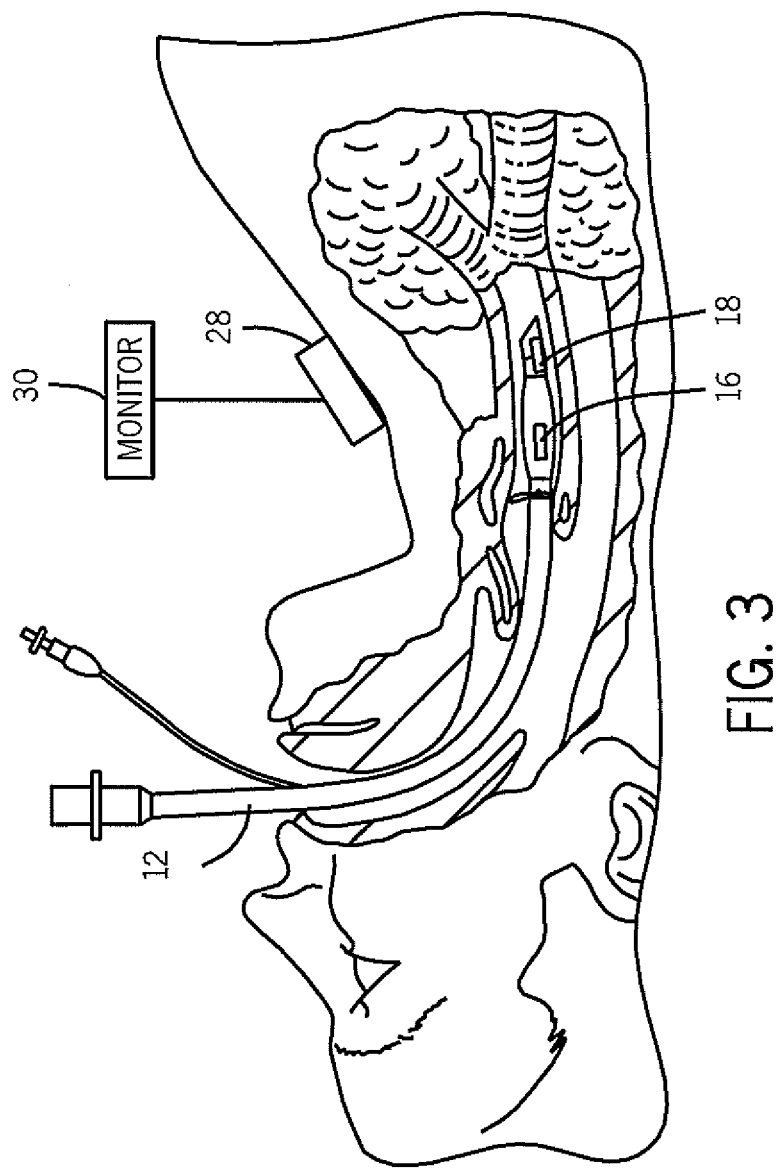
FIG. 3 is a side view of a tracheal tube inserted into a patient according to certain presently contemplated embodiments.

FIG. 3 is a side view of the tracheal tube 12 inserted into a patient's trachea. As shown, the receiver 28 may be positioned at a point outside the body, such as the sternal notch, as shown. The sternal notch, also referred to as the suprasternal notch or the jugular notch, is a space between clavicular notches. This location may be advantageous for transmitting and receiving signals to and from the signal sources 16 and 18 because of the absence of bone or thick intervening structures between the trachea and the sternal notch. Because the human body is partially conductive and composed of materials of different dielectric constants and characteristic impedances, signals may be absorbed or partly reflected rather than transmitted. Accordingly, selecting a site that minimizes such effects may improve signal quality. In addition, the signal quality may be improved if signal sources 16 and 18 are positioned on the face if the tracheal tube 12 closest to the sternal notch. Generally, this face corresponds with the inside of the curve of tube 12.

Figure 4:
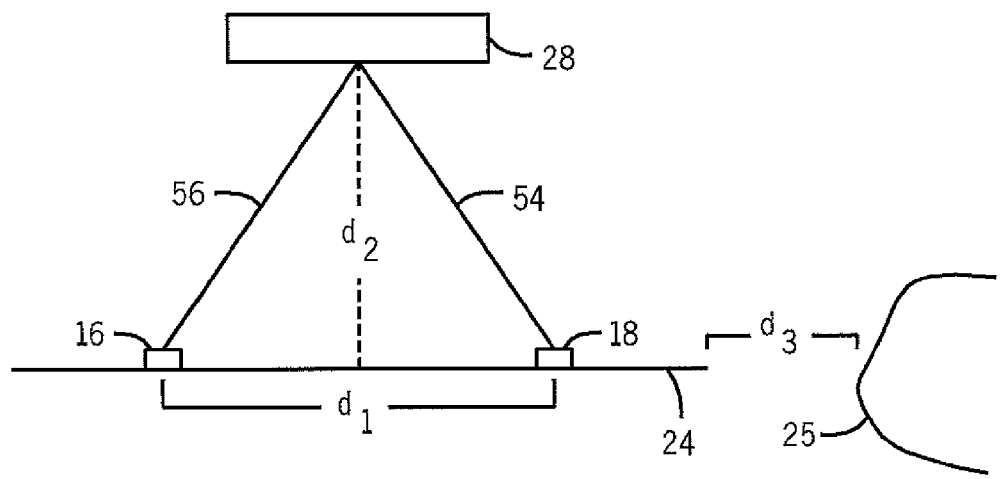
FIG. 4 is a schematic view of pressure signals received at a receiver.

As noted, the distance relationships between the receiver 28 and the signal sources 16 and 18 may be determined based on triangulation of the signals. FIG. 4 is a schematic view of these distance relationships. The distance $d_1$ between the signal sources 16 and 18 is known and may be stored in the monitor 30 or otherwise communicated as part of the calibration information. The unknown quantities for purposes of location determination may be the distance 56 between the signal source 16 and the receiver 28, and the distance 54 between the signal source 18 and the receiver 28. These distances may be estimated by any suitable triangulation techniques based on time of flight or intensity differences between the received signals. In certain embodiments, the distance $d_2$ between the receiver 28 (or the sternal notch) and the tube 12, e.g., the depth into the body, may be a known or estimated quantity.

In addition, a distance $d_3$ between the sternal notch and a carina 25 may also be known or estimated based on the patient's size and/or weight. When $d_3$ is known or estimated, the location of the distal end 24 of tube 12 relative to the carina 25 may be determined based on the distance from the distal end 24 to the sternal notch. When signal source 18 is located at the distal end 24 of the tube 12, determining the location of the signal source 18 may substitute for determining the location of the distal end 24. When the signal source 18 is near the distal end 24, a correction factor may account for any space between the signal source 18 and the distal end 24.

Figure 5:
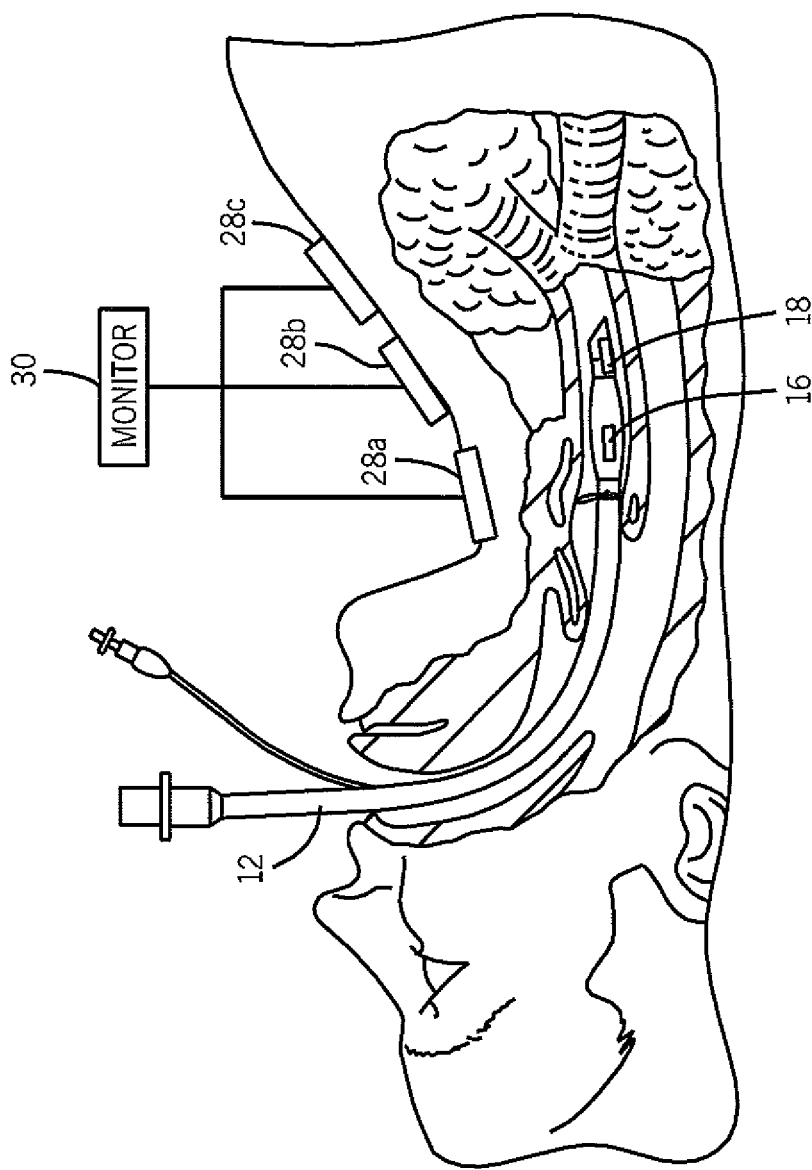
FIG. 5 is a side view of a tracheal tube arrangement including multiple receivers according to a presently contemplated embodiment.

Additional information may be obtained by using multiple receivers 28 (or transmitter/receivers) to collect additional signals from the signal sources 16 and 18, as shown in FIG. 5. For example, multiple receivers, shown as receivers 28a, 28b, and 28c, may be arranged along an axis that is substantially in-line with the patient's trachea that starts at the sternal notch and proceeds along the patient's chest. By using an axial arrangement, certain angle differences between the signal sources and the receivers may cancel out. In addition, in particular for time of flight differences, longer flight times may be more distinguishable with a longer measurement distance.

Figure 6:
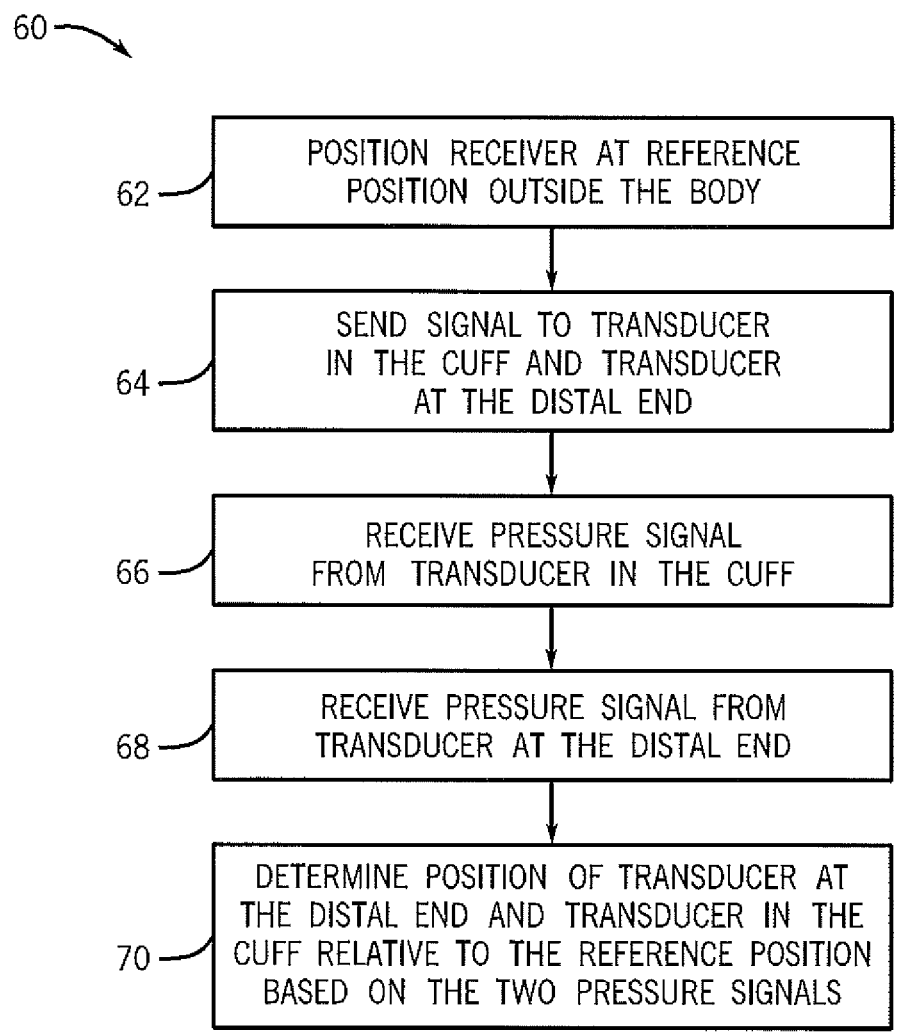
FIG. 6 is a flow diagram of a method of determining pressure and distance information from pressure signals.

FIG. 6 is a process flow diagram illustrating a method of determining pressure and location information from signal sources associated with the tracheal tube 12. The method is generally indicated by reference number 60 and includes various steps or actions represented by blocks. It should be noted that the method 60 may be performed as an automated procedure by a system, such as system 10. Further, certain steps or portions of the method may be performed by separate devices. For example, a first portion of the method 60 may be performed by a signal source 16 or a signal source 18, while a second portion of the method 60 may be performed by a monitor 30. The method 60 may be performed continuously or intermittently for long-term patient monitoring or at any appropriate interval depending on the particular situation of the intubated patient. Further, the steps of method 60 may be performed during insertion of the tracheal tube 12 into the patient.

According to the illustrated embodiment, the method 60 begins with positioned the receiver 28 at the reference position at step 62. In certain other embodiments, multiple reference positions may be used. The receiver, once positioned, may emit a signal through an associated transmitter, to activate the wireless functionality of the signal sources 16 and 18 at step 64. In the example in which the sources 16 and 18 are pressure transducers, the signal may be sent to a transducer positioned at a distal end of the cuff and a transducer positioned in the cuff. At step 66 the receiver 28 receives a signal from the signal source 18, and at step 68 the receiver receives a signal from the signal source 16. For example, the signal source 16 may be positioned in the cuff and the signal source 18 may be positioned at the distal end 20. Where the signal sources 16 and 18 are pressure transducers, the signals may include pressure data. The receiver may communicate the signals to the monitor 30, which may perform analysis of the pressure signals to determine location information at step 70. In addition, the monitor may determine pressure information from the signals.

A monitor 30 may use the location information to determine certain placement parameters to determine whether the tracheal tube 12 is correctly placed. Examples of placement parameters may include a calculated distance between a tube 12, the distal end 24 of the tube 12, or one or more of the signal sources 16 or 18, and an anatomical structure, such as a carina 25 or a sternal notch. In one embodiment, a placement parameter may be a determined distance from the distal end 24 to the sternal notch. For example, proper placement may be when the distance $d_2$ is as close as possible to the distance 54, indicating that the distal end 24 is substantially at the depth of the sternal notch. A proper placement may also reflect a determined distance between a distal end 24 and a carina 25. In other embodiments, the placement parameter may be a ratio of a calculated distance and an empirically derived or clinically measured distance associated with proper tube placement. It should be appreciated that there may be several empirically derived target distances, depending on the size, age, or gender of the patient. A target distance to which the measured distance may be compared may differ for adult men and adult women or children.

A placement parameter may also be an average or mean of multiple data points or measurements. A placement parameter may also include a graphical, visual, or audio representation of the tube/anatomical structure distance. For example, a placement parameter associated with proper placement may include green light indicated on a display or a short tone generated by a speaker associated with monitor 30. Similarly, a placement parameter associated with improper placement of the tube 12 may trigger an alarm, which may include one or more of an audio or visual alarm indication. In one embodiment, the alarm may be triggered if the placement parameter is, substantially less than or substantially greater than a predetermined value, or outside of a predetermined range.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of tracheal tube placement relative to anatomical structures in the trachea, but these techniques may also be utilized for the measurement and/or analysis of the placement of other suitable medical devices relative to other anatomical structures. For example, the present techniques may be utilized for the measurement and/or analysis of tracheal tubes relative to tracheal walls or the vocal cords. In addition, the present techniques may be employed in determining appropriate placement of any medical device, such as a stent, catheter, implant, feeding tube, cardiac device, drug delivery device, or pump. Rather, the various embodiments may cover all modifications, equivalents, and alternatives falling within the spirit and scope of the disclosure as defined by the following appended claims.

What is claimed is:

1. A method for determining placement of a tracheal tube in a subject comprising:
   receiving a first signal with a receiver from a first pressure transducer disposed in an inflatable cuff disposed on the tracheal tube in the subject, wherein the receiver is positioned at a reference location outside the subject;
   receiving a second signal with the receiver from a second pressure transducer disposed on the tracheal tube distal to the inflatable cuff;
   determining a cuff pressure from the first signal and a tracheal pressure from the second signal; and
   determining a placement parameter for the tracheal tube based upon triangulation of the first signal and the second signal.

2. The method of claim 1, comprising sending a signal to the first pressure transducer and the second pressure transducer with a transmitter when the receiver is positioned at the reference location outside the subject.

3. The method of claim 1, wherein the first signal and the second signal comprise radio frequency signals and wherein the receiver comprises a radio frequency receiver.

4. The method of claim 1, wherein the placement parameter is representative of a distance between the tracheal tube and an anatomical structure.

5. The method of claim 4, wherein the anatomical structure comprises a sternal notch or a carina.

6. The method of claim 5, comprising triggering an alarm or message when the distance between the tracheal tube and the sternal notch or the carina is less than or greater than a predetermined distance or when the distance between the tracheal tube and the sternal notch falls outside of a predetermined range.

7. The method of claim 1, wherein the steps are performed during intubation of the subject.

8. The method of claim 1, wherein the steps are performed after intubation of the subject.

9. A system for determining placement of a tracheal tube in a subject comprising:
   a tracheal tube comprising an inflatable cuff;
   a first pressure transducer disposed adjacent to a distal end of the tracheal tube;
   a second pressure transducer disposed in the inflatable cuff;
   a receiver adapted to be positioned at a reference location outside the subject, wherein the receiver is adapted to receive a first signal from the first pressure transducer and a second signal from the second pressure transducer; and
   a processor programmed with instructions for determining a placement parameter for the tracheal tube based upon triangulation of the first signal and the second signal.

10. The system of claim 9, wherein the tracheal tube comprises a curve along a length of the tube when the tube is not inserted in the subject, and wherein the first pressure transducer and the second pressure transducer are disposed on an inside face of the curve.

11. The system of claim 9, wherein the first signal and the second signal comprise radio frequency signals.

12. The system of claim 11, wherein the first signal comprises a different radio frequency than the second signal.

13. The system of claim 11, wherein the receiver is adapted to receive signals in a band comprising 402 MHz-405 MHz.

14. The system of claim 9, comprising an alarm configured to be triggered when the placement parameter indicates that the tracheal tube is at a predetermined distance from an anatomical structure.

15. The system of claim 9, wherein the processor is programmed with instructions for providing an indication when the receiver is correctly positioned at the reference location.

16. The system of claim 15, wherein the reference location comprises a sternal notch of the subject.

17. The system of claim 9, comprising a second receiver adapted to be positioned at a second reference location outside the subject.

18. The system of claim 17, comprising a third receiver adapted to be positioned at a third reference location outside the subject, wherein the first reference location, the second reference location, and the third reference location comprise an axis.

19. A device for determining placement of a tracheal tube in a subject comprising:
   a processor programmed with instructions for:

receiving a first pressure signal related to an inflatable cuff disposed on a tracheal tube from a receiver;

receiving a second pressure signal related to a location distal of the inflatable cuff on the tracheal tube from the receiver; and determining a placement parameter for the tracheal tube based upon triangulation of the first pressure signal and the second pressure signal.

20. The device of claim 19, wherein the processor comprises instructions for providing an indication of the placement parameter.

21. A method for determining placement of a tracheal tube in a subject comprising:

determining a first pressure at a distal end of the tracheal tube disposed in the subject with a first wireless pressure transducer disposed on the tracheal tube;

determining a second pressure inside an inflated cuff associated with the tracheal tube with a second wireless pressure transducer disposed in the inflated cuff;

receiving a first signal related to the first pressure and a second signal related to the second pressure with a receiver, wherein the receiver is positioned at a reference location outside the subject; and determining a placement parameter for the tracheal tube based upon triangulation of the first signal and the second signal.

22. The method of claim 21, comprising sending a signal to the first pressure transducer and the second pressure transducer with a transmitter when the receiver is positioned at the reference location outside the subject.

23. The method of claim 21, wherein the first signal and the second signal comprise radio frequency signals and wherein the receiver comprises a radio frequency receiver.

24. The method of claim 21, wherein the placement parameter is representative of a distance between the tracheal tube and an anatomical structure.

25. The method of claim 24, wherein the anatomical structure comprises a sternal notch or a carina.

* * * * *